(12) United States Patent
Loth et al.

(10) Patent No.: US 10,774,823 B2
(45) Date of Patent: Sep. 15, 2020

(54) DISPOSABLE CARTRIDGE FOR A PERISTALTIC MICRO PUMP AND A PERISTALTIC MICRO PUMP

(71) Applicant: TECHNISCHE UNIVERSITÄT BERLIN, Berlin (DE)

(72) Inventors: Andreas Loth, Berlin (DE); Ralf Förster, Berlin (DE)

(73) Assignee: Technische Universitat Berlin, Berlin (DE)

(*) Notice: Subject to any disclaimer, the term of this patent is extended or adjusted under 35 U.S.C. 154(b) by 356 days.

(21) Appl. No.: 15/486,676

(22) Filed: Apr. 13, 2017

(65) Prior Publication Data

US 2017/0298921 A1 Oct. 19, 2017

(30) Foreign Application Priority Data

Apr. 15, 2016 (DE) .................. 10 2016 004 947

(51) Int. Cl.
*F04B 43/12* (2006.01)
*F04B 43/00* (2006.01)
*A61M 5/142* (2006.01)

(52) U.S. Cl.
CPC ...... *F04B 43/0072* (2013.01); *F04B 43/1253* (2013.01); *F04B 43/1284* (2013.01); *A61M 5/14232* (2013.01); *A61M 2205/12* (2013.01)

(58) Field of Classification Search
CPC ............ A61M 5/14232; A61M 1/1039; A61M 2205/12; F04B 43/1238; F04B 43/1253; F04B 43/1276; F04B 43/1284; F04B 43/1292; F04B 19/006; F04B 43/12
USPC ..................................................... 417/477.2
See application file for complete search history.

(56) References Cited

U.S. PATENT DOCUMENTS

D264,134 S  *  4/1982  Xanthopoulos ............... 417/474
4,417,856 A  * 11/1983  Minissian ........... F04B 43/1276
                                                  417/477.7
4,735,558 A  *  4/1988  Kienholz ............ F04B 43/1284
                                                  417/477.2

(Continued)

OTHER PUBLICATIONS

W.E. Morf et al "Partial Electromosmotic Pumping in Complex Capillary Systems Part 1: Principles and General Theoretical Approach" Sensors, Actuators and Microsystems Laboratory, Institute of Microtechnology, University of Neuchâtel, 2001 Elsevier Science B.V. (2001).

(Continued)

*Primary Examiner* — Kenneth J Hansen
(74) *Attorney, Agent, or Firm* — Harness Dickey

(57) ABSTRACT

A disposable cartridge (20) for a peristaltic micro pump is disclosed. The cartridge comprises a housing (21) with an inlet connector (25) and an outlet connector (26). A fluid channel (23) extends in the housing (21) between the inlet and the outlet with a channel section (22) of the fluid channel (23) provided by a flexible tube (24). One or more openings are provided adjacent to the channel section (22) in the housing (21) allowing one or more pump engaging elements of a pump drive to engage the flexible tube (24), compressing the flexible tube (24) to pump fluid through the fluid channel (23). Sealing elements (31, 32) with double flange extensions (31a, 31b) having a first inner flange (31a, 32a) and a second outer flange (31b, 32b) are provided to seal at the connectors (25, 26) and fix the tube (24) in the housing (21).

9 Claims, 13 Drawing Sheets

(56) References Cited

U.S. PATENT DOCUMENTS

Figure 1:
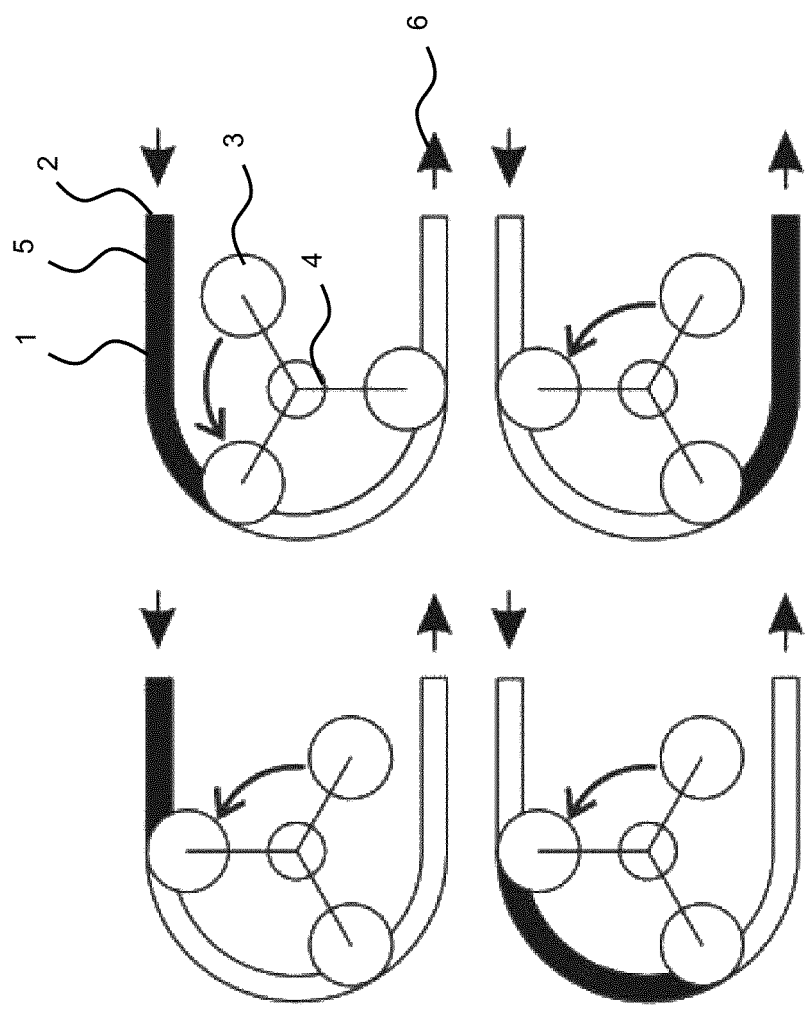

| | | | |
|---|---|---|---|
| 6,468,059 B2 * | 10/2002 | Haser | A61M 3/0258 |
| | | | 417/477.1 |
| 2004/0265154 A1 * | 12/2004 | McDowell | F04B 43/009 |
| | | | 417/474 |
| 2008/0138218 A1 * | 6/2008 | Miyazaki | A61M 5/14228 |
| | | | 417/410.3 |

OTHER PUBLICATIONS

W. E. Morf et al "Partial Electroosmotic Pumping in Complex Capillary Systems Part 2: Fabrication and Application of a Micro Total Analysis System Suited for continuous Volumetric Nanotitrations" Sensors, Actuators and Microsystems Laboratory, Institute of Microtechnology, University of Neuchâtel, 2001 Elsevier Science B.V. (2001).

C. R. Tamanaha et al "Hybrid Macro-Micro Fluidics System for a Chip-Based Biosensor" 2002 IOP Publishing Ltd, (2002).

Jeffrey D. Zahn et al "Continuous On-Chip Micropumping for Microneedle Enhanced Drug Delivery" Biomedical Microdevices 6:3, 183-190 (2004).

Beom S. Lee et al "Fully Integrated Lab-On-A-Disc for Simultaneous Analysis of Biochemistry and Immunoassay From Whole Blood", Lab Chip, 2011, 11, 70 (2011).

T. Ohori et al "Partly Disposable Three-way Microvalve for a Medical Micro Total Analysis System" 1998 Elsevier Science A. A. (1998).

J. Melin et al "Microfluidic Large-Scale Integration: The Evlution of Design Rules for Biological Automation", Annu. Rev. Biophys. Biomol. Struct. 2007 36:213-31 (2007).

* cited by examiner

DISPOSABLE CARTRIDGE FOR A PERISTALTIC MICRO PUMP AND A PERISTALTIC MICRO PUMP

CROSS-REFERENCE TO RELATED APPLICATIONS

This application claims priority to German Application No. 102016004947.2 filed Apr. 15, 2016. The disclosure of the above application is incorporated herein by reference.

The present disclosure refers to a disposable cartridge for a peristaltic micro pump and a peristaltic micro pump.

BACKGROUND

Several applications in medicine, biochemistry or chemical engineering require the handling of small precise amounts of liquids. Blood or rare substances have to be analyzed or processed in ever shorter times. Disposable bio chips called LOC (Lab on a chip), μTAS (micro Total Analysis Systems) or DNA micro arrays devices are mostly the key element of a fast and reliable analysis. The exact control of the process liquids is vital for the whole process. Two main methods are usual to achieve high dosage accuracy. It must be also subdivided between internal or external control or generation. The first common used method is to use pumps that deliver the necessary amount directly. Syringe pumps or small gear pumps are reliable and widely accepted external solutions. For on chip pressure generation solutions like electroosmosis (Morf et al., *Sensors and Actuators B: Chemical*, vol. 72(3), pp. 266-272, 2001), (Guenat et al., *Sensors and Actuators B: Chemical*, vol. 72(3), pp. 273-282, 2001), applying of static pressure on internal membrane reservoirs (Tamanaha et al., *Journal of Micromechanics and Microengineering*, vol. 12(2), N7, 2002), thermally created gas bubbles (Handique et al., *Analytical Chemistry*, vol. 73(8), pp. 1831-1838, 2001), (Zahn et al., *Micro Electro Mechanical Systems*, The 14th IEEE International Conference on, pp. 503-506, 25-25 Jan. 2001) or the "Lab Disc" approach (Lee et al., *Lab on a Chip*, vol. 11(1), pp. 70-78, 2011), (Zengerle et al., SELECTBIO 2015 Lab-on-a-Chip Broadcast Event, 16.06.2015) can be found. The second main method is the control of the delivered volumes by using micro valves, which can be on (Ohori et al., *Sensors and Actuators A: Physical*, vol. 64(1), pp. 57-62, 1998), (Melin et al., *Annual Review of Biophysics and Biomolecular Structure*, vol. 36(1), pp. 213-231, 2007) or off chip (Bürkert, Buerkert Product overview 05 Micro-Fluidics, Ingelfingen, 2010). Combinations of both methods can also be found and an implementation of flow sensors is possible.

A thorough cleaning of the devices Is of great importance in order to prevent contaminations. The step of changing the main components is often time intensive but better solutions exist for valves and pumps (Loth et al., *Nano/Micro Engineered and Molecular Systems (NEMS)*, IEEE 10th International Conference on, pp. 9-14, 7-11 Apr. 2015).

With regard to pumps, a major problem for modular systems or small size applications is the large size of external components. They often have a great Internal or dead volume that prevents the integration into small complex systems with high density like e.g. micro fluidic chips. An on-chip pressure generation cannot often be achieved by scaling down conventional macroscopic pumping principles, because of manufacturing, fluid dynamical or material problems in combination with decontamination and costs. In some cases scaling is possible if modifications are carried out, as will be presented.

SUMMARY

It is an object to provide a disposable cartridge for a peristaltic micro pump and a peristaltic micro pump which allow flexible use of the pump in different applications.

For solving the object, a disposable cartridge for a peristaltic micro pump and a peristaltic micro pump according to the independent claims 1 and 13, respectively, are provided. Alternative embodiments are disclosed in dependent claims.

According to an aspect, a disposable cartridge for a peristaltic micro pump is provided, comprising: a housing; a inlet provided on the housing and comprising an inlet connector; an outlet provided on the housing and comprising an outlet connector; a fluid channel extending in the housing between the inlet and the outlet; a channel section of the fluid channel, the channel section provided by a flexible tube; one or more openings provided adjacent to the channel section in the housing in such a way that one or more pump engaging elements of a pump drive can engage with the flexible tube through the opening for compressing the flexible tube in a pumping process for pumping a fluid through the fluid channel; and a mounting device provided on the housing for detachably mounting the housing in a peristaltic micro pump housing.

According to another aspect, a peristaltic micro pump comprising a disposable cartridge is provided.

The flexible tube may be detachably received in a tube recess of the housing. Alternatively, the flexible tube may be non-detachably in the housing. It may be mounted at the time of assembling the disposable cartridge. The disposable cartridge may be disposed after use without removing the flexible tube.

The flexible tube may comprise at least one of a curved tube section and a linear tube section configured to engage with the one or more pump engaging elements providing a linear pump element arrangement and a rotating pump element arrangement, respectively. The curved section may be provided in a curved recess of the housing. The curved section may extend over a half circle.

The housing may comprise a curved housing section for receiving one or more engaging elements of the rotating pump element arrangement provided on a rotor within the curved housing section, wherein a first opening is provided adjacent to the curved section in the rotor recess.

The first opening may be provided on a narrow side of the housing.

The housing may comprise a linear recess for receiving the linear tube section, wherein a second opening is provided adjacent to the linear tube section. By means of the alternative tube sections the disposable cartridge may be configured at least one of a linear pump element arrangement and a rotating pump element arrangement. Also, a combination of at least one linear pump element arrangement and at least one rotating pump element arrangement may be provided.

The second opening may be provided on a flat side of the housing.

The flexible tube may comprise a plurality of flexible sub-tubes, each of the flexible sub-tubes received in a separate sub-recess of the housing and providing for a channel sub-section of the fluid channel.

The flexible tube may comprise at least one sealing element on each of opposite ends. The one or more sealing elements may comprise a flange extension or section in at least one end section.

The flexible tube may be form-fitted received in the recess.

The flexible tube may comprise a flange extension in at least one end section or in both end sections.

The disposable cartridge may further comprise a fluid reservoir provided in the housing and having a fluid connection to the fluid channel.

With regard to the peristaltic micro pump comprising the disposable cartridge, the alternative embodiments described above may apply mutatis mutandis.

A novel disposable high pressure peristaltic micro pump is disclosed which allows a precise dosing of single volumes in the nanolitre range. The flexible tube is integrated into a single use or disposable cartridge, which offers numerous advantages. A high pressure can be generated, while a small internal volume gives opportunity to handle expensive or rare fluids. Its small size allows the implementation into biochips or micro fluidic systems. A standalone solution can be connected to semi flexible tubes or pipes. The fluidic properties of the pump and the achievable maximum pressure have been determined. The fatigue resistance of the cartridge has been verified. Its simple structure offers the potential for mass production.

With the disposable cartridge a modular assembly for a peristaltic micro pump may be provided, wherein the peristaltic micro pump comprises the disposable cartridge module and a driving module provided with a motor and one or more pump engaging elements.

With regard to the disposable cartridge which may be a modular assembly itself, at least some of the elements, such as the housing or the flexible tube, may be provided as casted elements made of plastic.

The disposable cartridge may be integrated into a microchip, for example as part of a LOC (Lab on a chip) or μTAS (micro Total Analysis Systems) device.

Connectors may be provided, among others, for bayonet mount connections, self-securing plug connections, threaded connections or combinations thereof. Alternatively or additionally, one or more connectors may be fixed to elements such as a reservoir, a valve, a nozzle, or a flexible or rigid tube.

As another alternative, the fluid channel extending in the housing as whole may be comprised of the flexible tube fixed in the housing. The flexible tube may protrude from the housing. Protruding ends may provide for connecting to other elements. One end of the flexible tube may protrude from the housing while the other end is connected to a reservoir fixed to the housing.

The disposable cartridge may be provided as a stackable cartridge in such a way that one or more pump engaging elements may engage with a plurality of disposable cartridges to form a plurality of peristaltic micro pumps.

DESCRIPTION OF EMBODIMENTS

Figure 2:
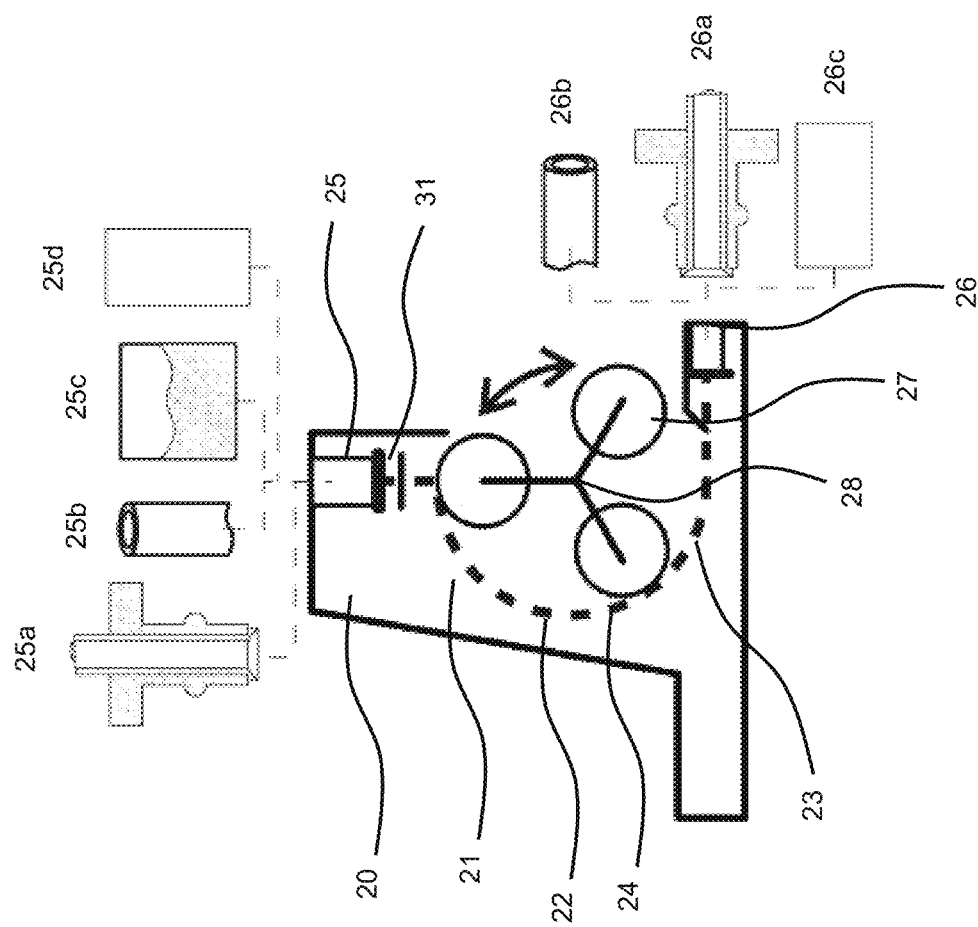
Figure 3:
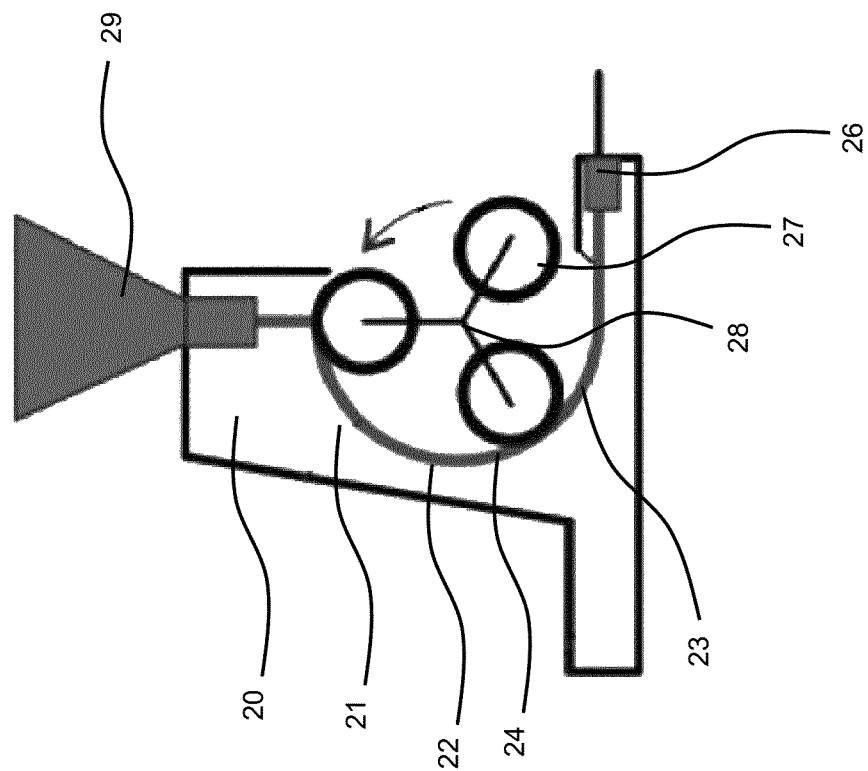
Figure 4:
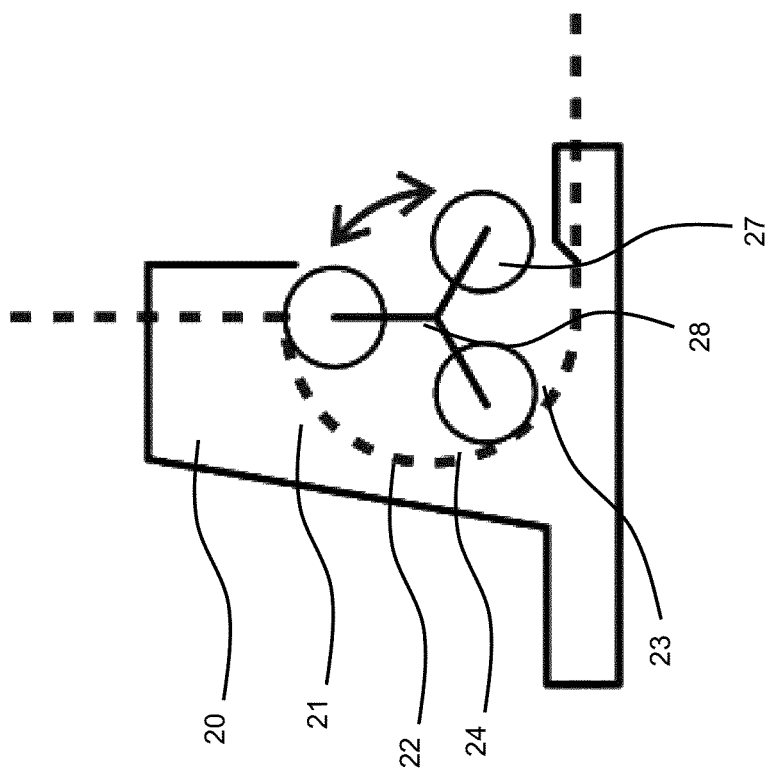
Figure 5:
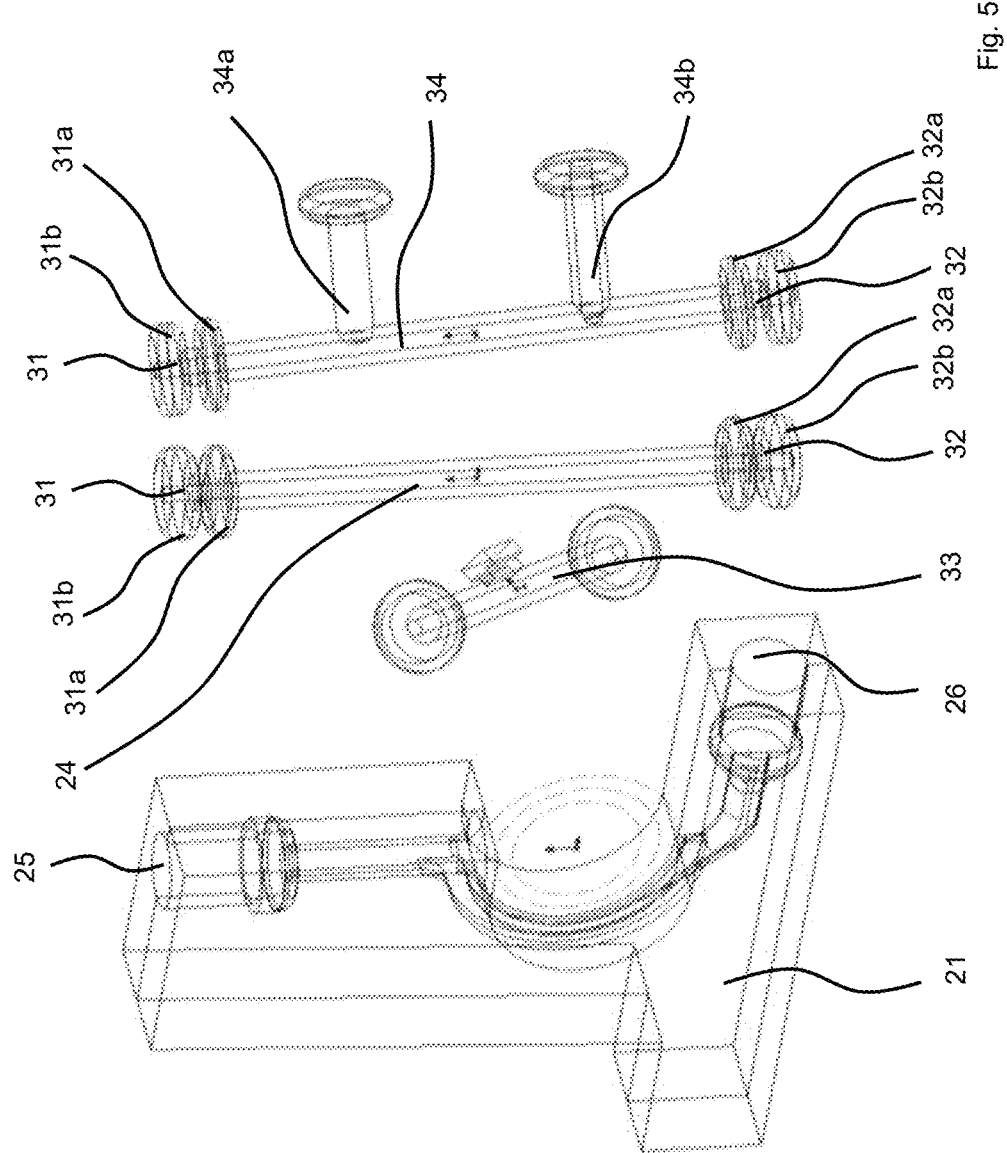
Figure 6:
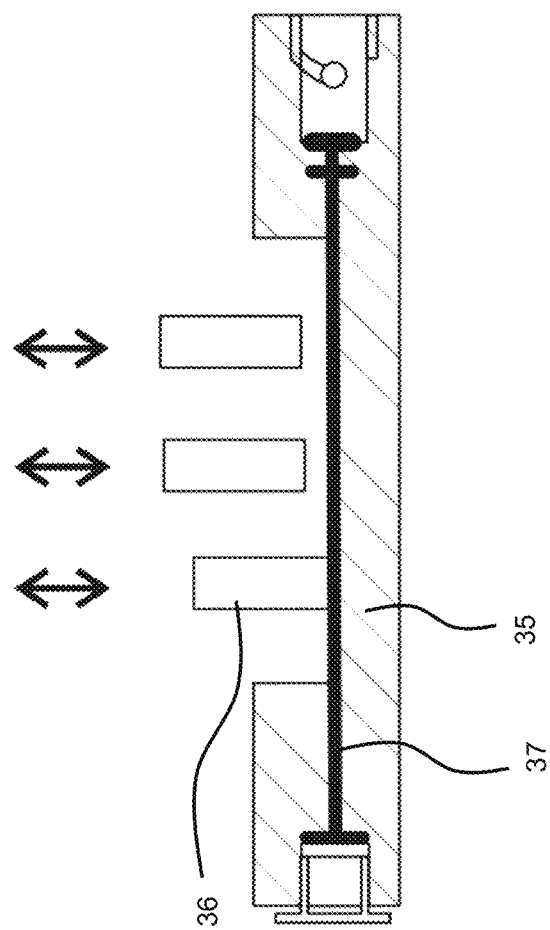
Figure 7:
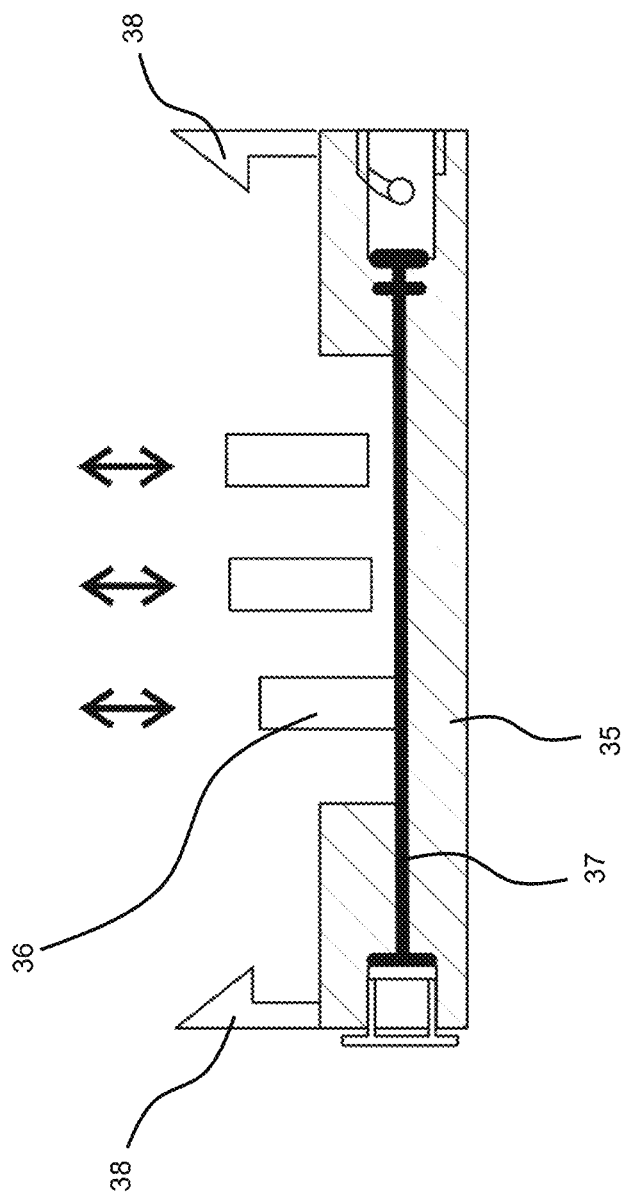
Figure 8:
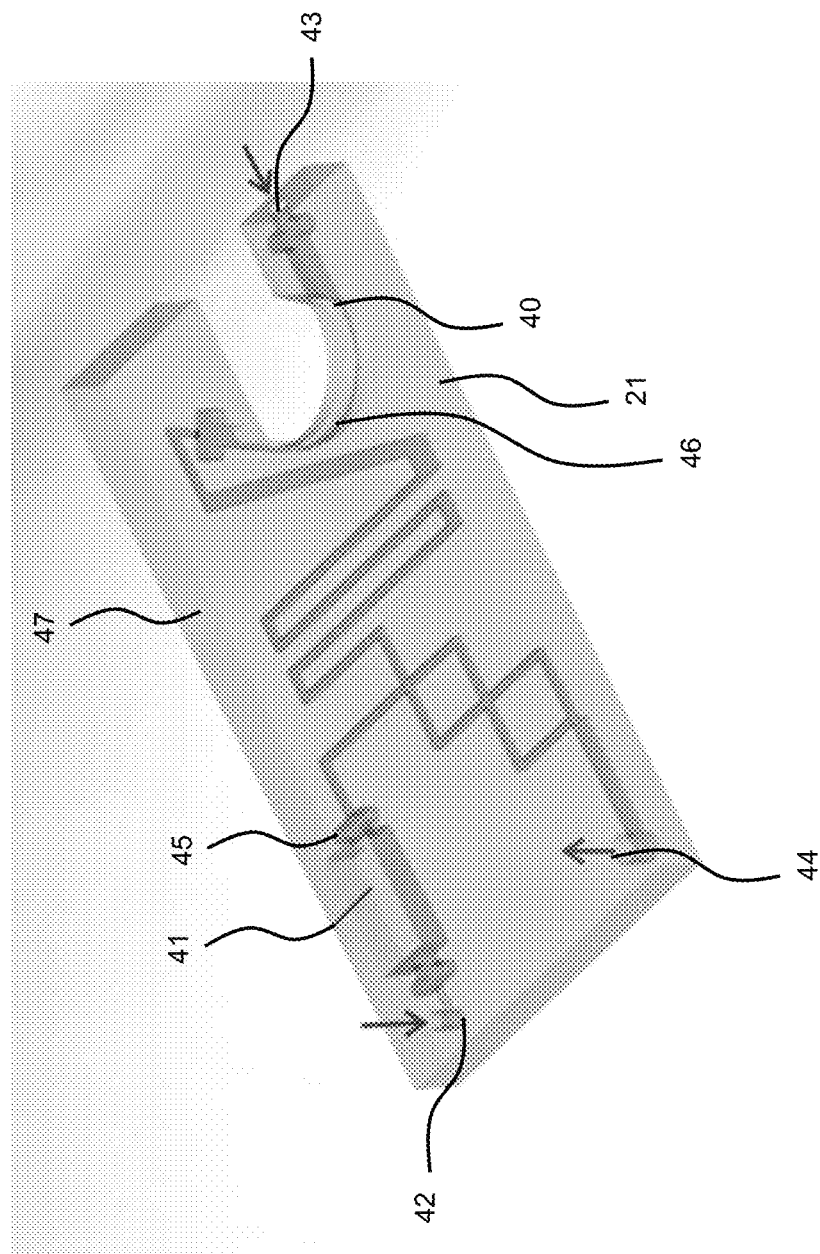
Figure 9:
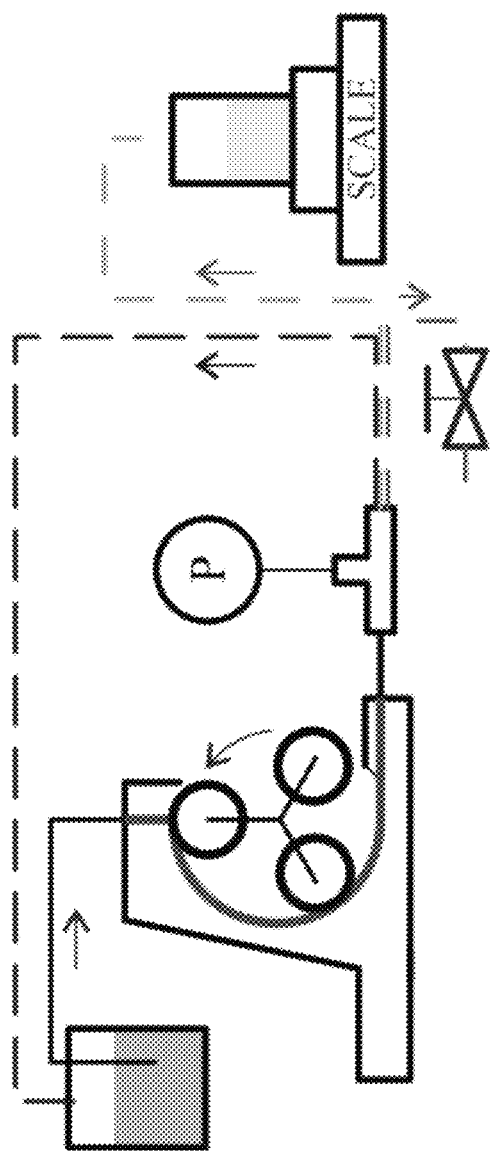
Figure 10:
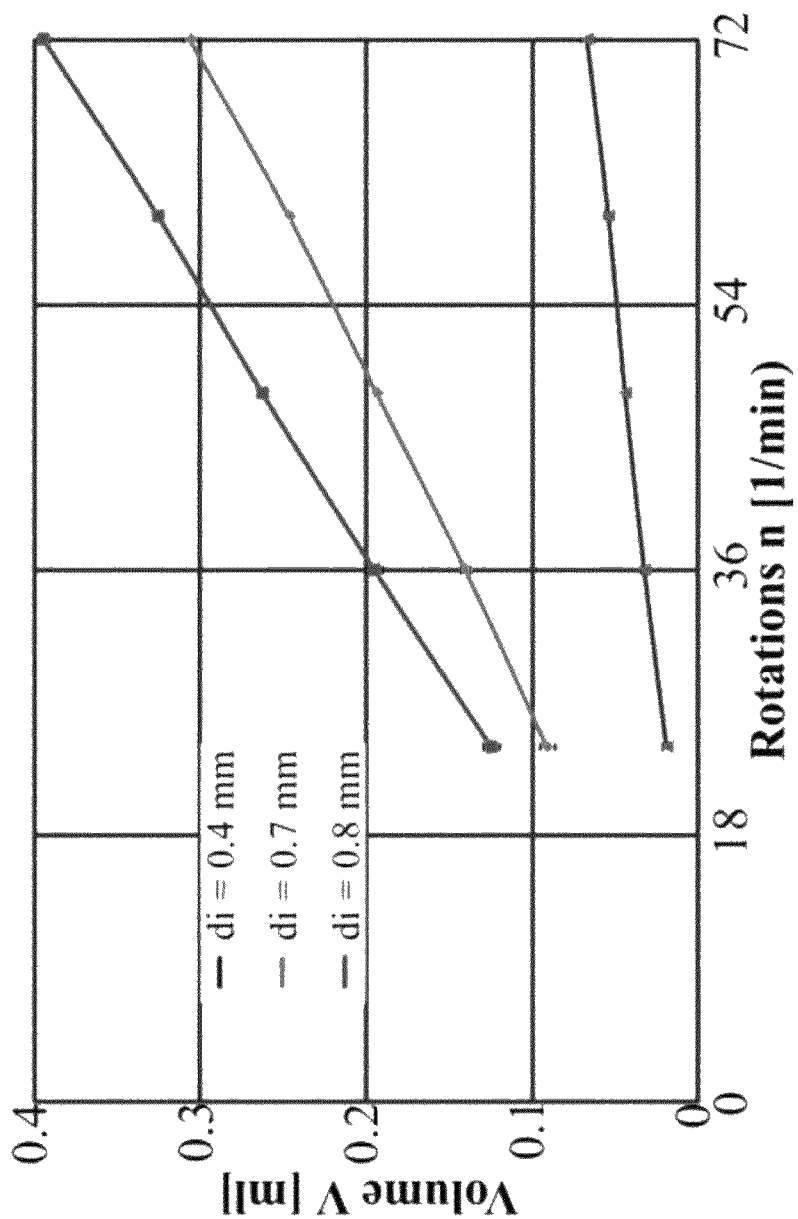
Figure 11:
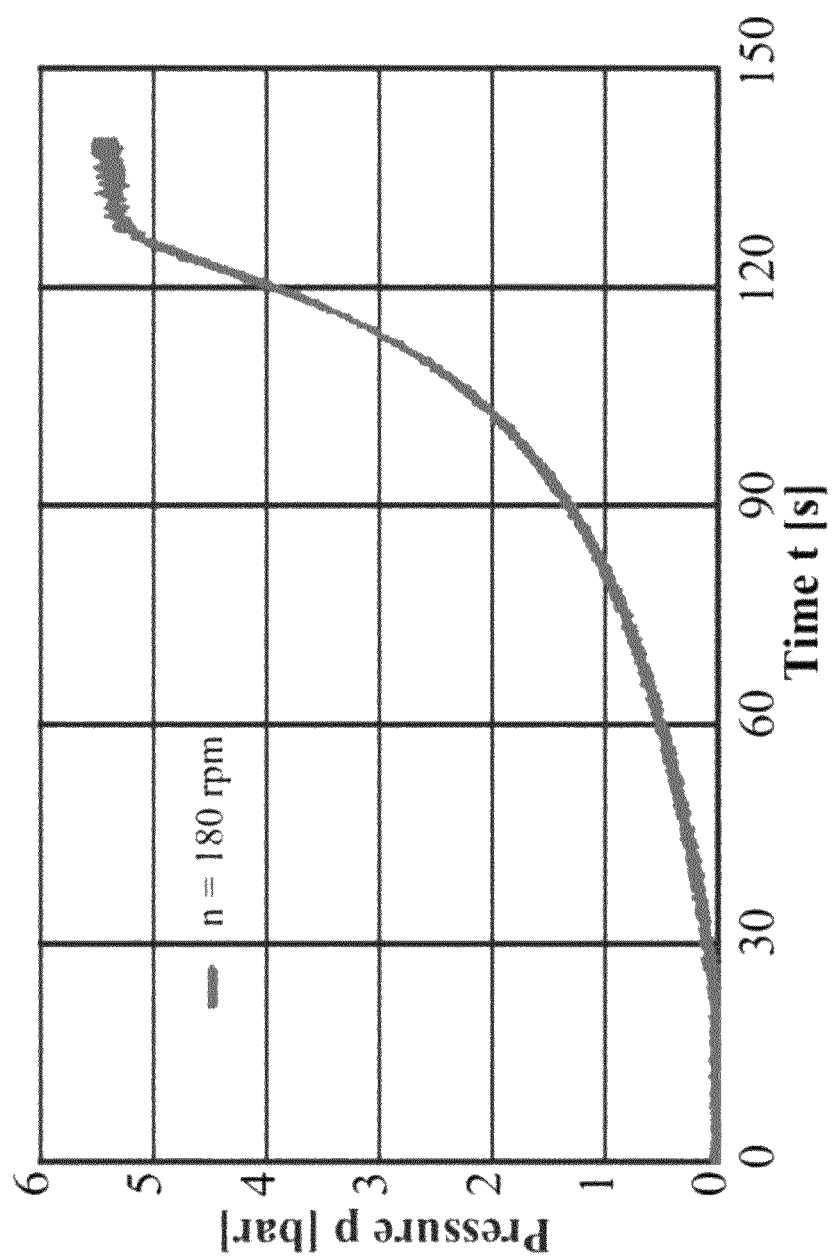
Figure 12:
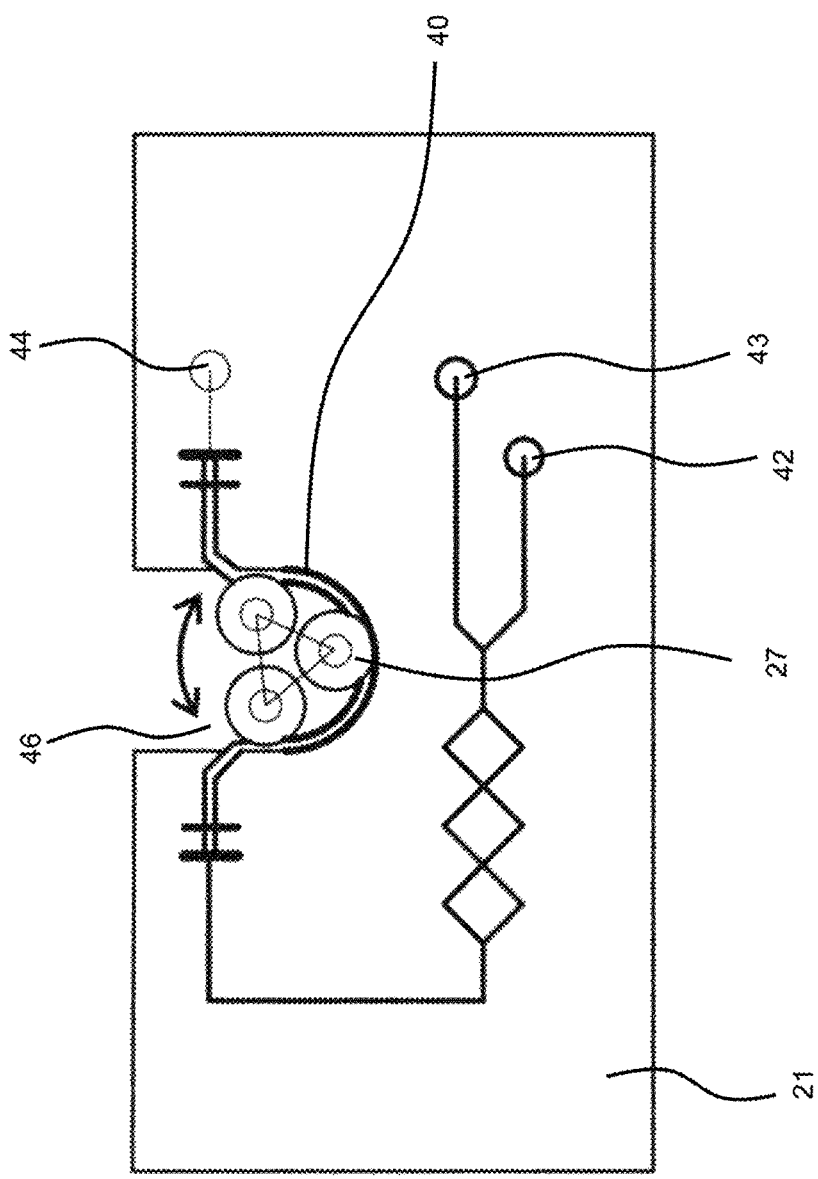
Figure 13:
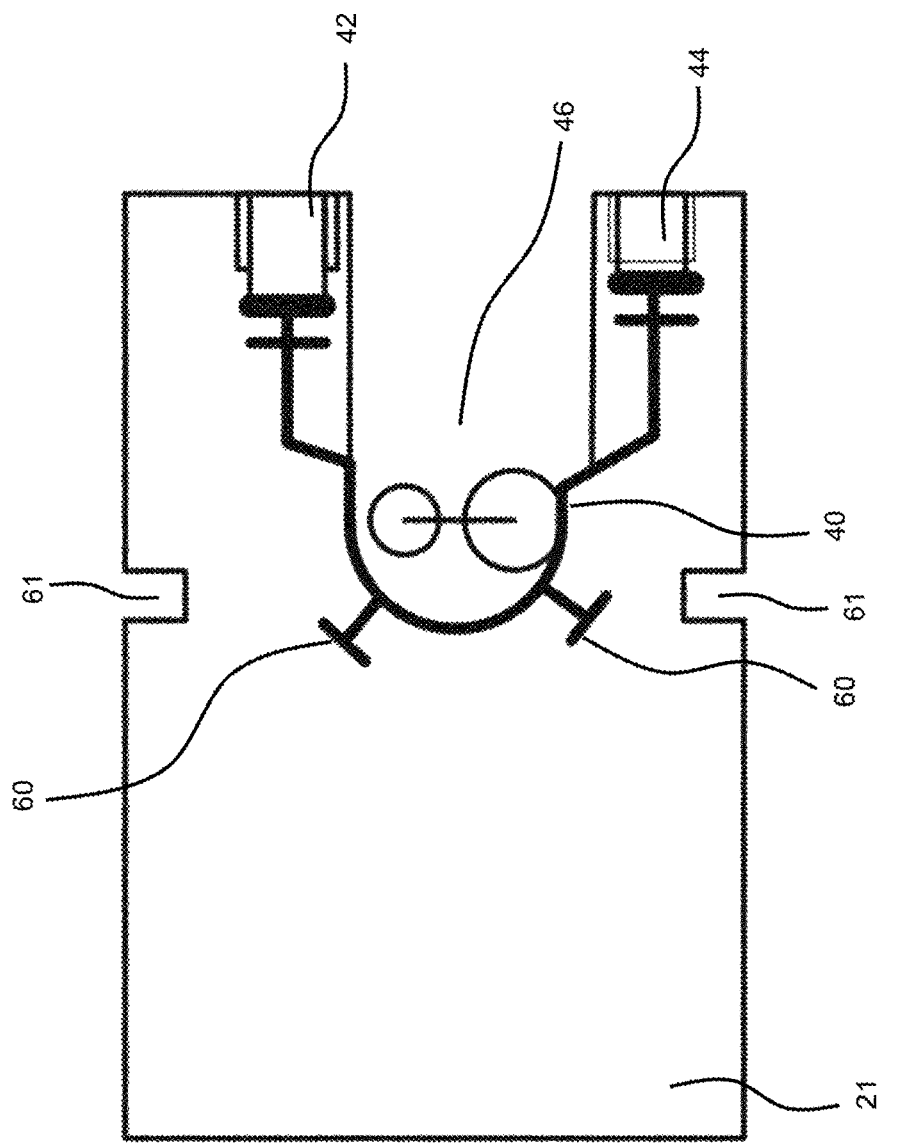

Following, further embodiments are described with reference to figures. In the figures show:

FIG. 1 a schematic representation of working principles of a standard peristaltic pump;

FIG. 2 a schematic representation of a disposable cartridge for a peristaltic micro pump provided with a channel section of a fluid channel, the channel section provided by a flexible tube, and an outlet connector and an Inlet connector;

FIG. 3 a schematic representation of another disposable cartridge for a peristaltic micro pump provided with a channel section of a fluid channel, the channel section provided by a flexible tube, and an outlet connector and an inlet connector;

FIG. 4 a schematic representation of a further disposable cartridge for a peristaltic micro pump provided with a channel section of a fluid channel, the channel section provided by a flexible tube, wherein the flexible tube provides for connecting elements;

FIG. 5 a schematic representation of an assembly set of elements for a disposable cartridge for a peristaltic micro pump;

FIG. 6 a schematic representation of a linear pump element arrangement configured to engage with a linear channel section of a fluid channel of a peristaltic micro pump, the linear channel section provided by a flexible tube;

FIG. 7 a schematic representation of an alternative linear pump element arrangement configured to engage with a linear channel section of a fluid channel of a peristaltic micro pump, the linear channel section provided by a flexible tube;

FIG. 8 a schematic representation of a disposable cartridge for a peristaltic micro pump provided with two channel sections of a fluid channel, the channel sections each provided by a flexible tube (micro fluidic mixing chip);

FIG. 9 a schematic representation of a measurement setup;

FIG. 10 a graphical representation of the low rate depending on inner tube diameter (water);

FIG. 11 a graphical representation of the maximum pressure measurement;

FIG. 12 a schematic representation of a disposable cartridge for a peristaltic micro pump provided with a curved channel section of a fluid channel; and FIG. 13 a schematic representation of a further disposable cartridge for a peristaltic micro pump provided with a curved channel section of a fluid channel.

A peristaltic micro pump having a disposable cartridge is described in further detail by referring to FIG. 1 to 7. The peristaltic micro pump can be provided as a standalone device or a device for integration into different kinds of micro fluidic chips. It provides a precise dosage of small volumes and can be easily discarded after use.

FIG. 1 shows a schematic representation of working principles of a standard peristaltic pump. There is a channel section 1 of a fluid channel, the channel section provided by a flexible tube. A fluid to be pumped is fed to in inlet 2. Pump engaging elements 3 are provided on a rotor 4. The pump engaging elements 3 are provided as rollers. A pumping sequence is shown in FIG. 1. While turning the rotor 4, the pump engaging elements 3 enclose a discrete amount of liquid 5 inside channel section 1 and move this from the Inlet 2 to an outlet 6 periodically (II-IV). Before a pump engaging element 3 reaches the outlet 6, a next pump engaging elements 3 already closed the inlet 2 (III) and prevents the backflow.

The transport is discontinuous and pressure fluctuations occur. The tube can be aligned in a half circular shape from greater 90 to over 180 degrees, depending on the number of pump engaging elements 3. Linear alignments are also possible (see FIG. 6). Here the fluid transport is generated by mechanical "fingers" or cams providing for (linear) pump engaging elements.

This pumping principle allows also the transport of shear stress sensitive materials like cells or suspensions. The pulsation can be adjusted by adapting the tube diameter, number of rollers and different tube materials. Pressure chambers or vessels as damping elements may be provided in an alternative.

FIG. 2 to 4 show schematic representations of a disposable cartridge 20 for a peristaltic micro pump provided with a housing 21. In the housing 21, a channel section 22 of a fluid channel 23 is provided, the channel section 22 provided by a flexible tube 24.

Referring to FIG. 2, on the housing 21, the disposable cartridge 20 comprises an inlet connector 25 and an outlet connector 26. When the disposable cartridge 20 is assembled in a peristaltic micro pump, the flexible tube 24, for pumping a fluid, is to engage with a plurality of pump engaging elements 27 provided on a rotor 28. In an alternative embodiment, there may be a single pump engaging element only.

Referring to FIG. 3, a schematic representation of another disposable cartridge 20 for a peristaltic micro pump is shown. A fluid reservoir 29 is connected to the inlet connector 25. The fluid reservoir 29 may be fixed to the housing 21, thereby, in some alternative embodiment substituting the inlet connector 25. In an alternative, the fluid reservoir 29 may be detachably connected to the inlet connector 25. The fluid reservoir 29 may be provided in the peristaltic micro pump itself, therefore, not being an element of the disposable cartridge 20.

The plurality of pump engaging elements 27 provided on the rotor 28 is provided in a curved housing section 30.

As shown FIG. 2, the flexible tube 24 comprises at least one sealing element 31 at the inlet and the outlet connectors 25, 26. Sealing elements provided on one end or both ends of the flexible tube 24 may be provided with double flange extensions (see FIG. 5).

As can be seen in FIG. 2, the inlet and/or the outlet connectors 25, 26 may be provided to couple with different connecting elements. The inlet connector 25 may be provided for coupling with a bayonet mount 25a containing a pipe or flexible tube. Alternatively, a flexible tube 25b may be fixed in the cartridge. As a further alternative, a reservoir 25c may be attached detachably or fixed at inlet connector 25. Other elements 25d may be provided fixed at or to be connected with inlet connector 25. Also, outlet connector 26 may be provided to couple with a bayonet mount 26a containing a pipe or flexible tube, may be fixed to a flexible tube 26b, or may be provided with other elements 26c fixed at the outlet connector 26 or connect-able thereto. The other elements 25d, 26c may include, for example, valves.

Referring to FIG. 4, a schematic representation of a further disposable cartridge 20 for a peristaltic micro pump is shown. The flexible tube 24 itself provides for the inlet connector 25 and the outlet connector 26.

In the alternative embodiments shown, the pump engaging elements 27 on the rotor 28 comprise three rollers. There may be more than three pump engaging elements 27 in an alternative embodiment.

The disposable cartridge 20 comprises an integration of the flexible tube 24 and the inlet connector 25 and the outlet connector 26 instead of a tubing only.

FIG. 5 shows a schematic representation of an assembly set of elements for a disposable cartridge for a peristaltic micro pump. The flexible tube 24 to be detachably received in the housing 21 comprises sealing elements 31, 32 on both ends, the sealing elements 31, 32 provided with flange extensions. In an alternative, there is only a single flange extension on the ends. There are a second flexible tube 33 and a third flexible tube 34 also to be detachably received in the housing 21.

If the fluid has to be changed or the flexible tube 24, 33, 34 is worn, the inlet connector 25 and the outlet connector 26 are disconnected and the whole disposable cartridge 20 with flexible tube 24, 33, 34 can be removed. The big advantage of this approach is the possibility to use different materials for tubing inside the pump and for the connected elements like pipes, as smaller peristaltic pumps use a single tube from reservoir through the pump to the outlet. Even rigid pipes of stainless steel or PTFE (polytetrafluorethylene) tubing can be connected to the disposable cartridge 20. The internal volume may be very low, for example, 1.59 to 11.31 µl (inner diameter $d_i$=0.3-0.8 mm). Another advantage is the integration of the sealing elements 31, 32 at the ends of the flexible tubes 24, 33, 34, which improves connectivity.

Alternatively, the flexible tube may be fixed in the housing during assembly and not be changed afterward.

Sealing elements 31, 32 may be provided with double flange extensions 31a, 31b; 32a, 32b. In this case, a first, inner flange 31a, 32a serves to fix the flexible tube 24, 33, 34 and may also serve to prevent adhesives from spreading. Second, outer flange 31b, 32b then serves to seal the connection at connector 25, 26 and also to fix the tube in the housing 21.

Flexible tube 34 may be provided with holding elements 34a, 34b. A holding element 34a may be provided without opening and is formed to be received by a corresponding cavity in housing 21 to prevent flexible tube 34 from moving or twisting when engaged by pump engaging elements. Alternatively, holding element 34b may be provided with an additional fluid canal.

FIG. 6 shows a schematic representation of a linear pump element arrangement 35 comprising pump engaging elements 36 configured, for pumping, to engage with a linear channel section 37 of a fluid channel of a peristaltic micro pump, the linear channel section provided by a flexible tube.

FIG. 7 is a schematic representation of an alternative linear pump element arrangement 35. In this embodiment, pump element arrangement 36 is provided with engagement hooks 38 for coupling to a linear peristaltic micro pump.

In the exemplary embodiments of FIGS. 6 and 7, linear pump element arrangement 35 is shown with a plug connection on the left side and a bayonet mount on the right side.

FIG. 8 shows a schematic representation of a disposable cartridge for a peristaltic micro pump provided with two channel sections 40, 41 of a fluid channel, the channel sections 40, 41 each provided by a flexible tube (micro fluidic mixing chip). It may be provided as a micro fluidic mixing chip (e.g. dimensions of 20×40 mm). The two channel sections 40, 41 provide for a curved tube section and a linear tube section configured to engage, through a respective opening in the housing, with the pump engaging elements providing a rotating pump element arrangement (see FIG. 2 to 4) and a linear pump element arrangement (see FIGS. 6 and 7), respectively.

The presented approach allows the simple integration of a tube and therefore a peristaltic micro pump into a µTAS device (TAS—Total Analysis System). FIG. 7 shows an embodiment with a linear flexible tube alignment geometry and a circular flexible tube alignment geometry, both approaches in one device for comparison. There are two inlet ports 42, 43 which allow the attachment of external tubes or reservoirs. The processed volume leaves the device through an outlet port 44. The linear actuator (pump engaging elements) operates the linear flexible tube section 40 from above through an opening 45 in the upper part of the chip housing. The rotor of the circular pump swings into another opening 46 of the chip housing to actuate the curved flexible tube section 40 of the fluid channel 47 provided in the housing.

Following, further aspects described with regard to examples are described.

Materials

Suitable materials for the bodies of the housing of the disposable cartridge 20 are polymers that can be used in injection molding, e.g. poly(methyl methacrylate) (PMMA), cyclic olefin copolymer (COC), polycarbonate (PC). Another requirement is the possibility of a bonding step afterwards, thermally or by adhesives. The on chip versions can be additionally made of silicon and glass, resulting in different mechanical rigidity, chemical resistance and biocompatibility.

Test bodies and structures for the disposable cartridge 20 were milled on a CNC milling machine (HEM 500, GF) with ball mills and end mills of 0.3-3.0 mm diameter. A batch of four test bodies was machined from one side on a plastic sheet. Then the single half bodies were separated. Different sample bodies were made of two different high tech PMMA (polymethylmethacrylat) types with excellent homogeneity in structure and height (Hesaglas HL/VOS, TOPACRYL, Switzerland). Main difference between the polymers is their grade of cross linking, interesting for the bonding step of the two half shells.

In the next preparation step, the flexible tube was inserted into one side and the other side was added. The connection was secured by adhesives (Loctite 3301, Henkel and ACRIFIX 1R 0192, Evonik) or thermal bonding. The thread (M3) for the fluid connectors of the evaluation samples was implemented finally.

Self-casted flexible tubes were made of the two component LSR silicone (liquid silicone rubber) QP1-70 (Dow Corning Corporation, Midland). The QP1 silicones are HTC-silicones (High Temperature Curing) that need 150° C. for curing (Dow Corning, Product Information http://www2.dowcoming.com/Data Files/090007c8803 586b0.pdf, acquired 15.08.2012). For manual manufacturing refer to (Loth et al., *Key Engineering Materials*, vol. 611-612, pp. 876-882, 2014). The inner diameter of these tubes was set between 0.3 and 0.8 mm with an outer diameter of $d_o$=1.2 mm.

Testing liquids were dionized water and a glycerine-water mixture (60/40 g). This proportion leads to a dynamic viscosity of 12 mPas, which correlates with previous tested DNA solutions (Loth, Entwicklung von Verfahren und Applikatoren für den intradermalen Wirkstoffeintrag, PhD-Thesis, Technische Universität Berlin, 2011.). The viscosity was measured with a RheolabQC rotational rheometer (Anton Paar, Austria).

PTFE (polytetrafluorpthylene) and silicone were chosen as tube materials for the connection or pipes. The tubes (0.8 mm×1.6 mm, Bohlender), (1.02 mm×2.16 mm, Silastic Lab Tubing, Dow Corning) were fixed with cyanoacrylate inside the fluid connectors.

The micro rotor group consists of the main rotor part made of brass, three stainless steel pins 1×5 mm and rollers 2×2.95 mm. Brass and PEEK were used as roller materials.

Methods

The arrangement prepared was used as key element to determine the characteristics of the peristaltic micro pump. It consists of the tube cartridge (not shown), the rotor with rollers, the a rotor clamping, a clutch to connect motor and rotor and a base plate.

A pressure sensor (CTE 8025GY0, sensortechnics) different PTFE and silicone tubes with connectors, a high precision scale (AE 160, Mettler) were the testing periphery. A servo motor with encoder (1717T006S R IE2-16, Faulhaber) allows a maximum circumferential Inlet speed of 5.000 rpm due to the 66:1 gear. The speed was adjusted via the motion controller (MCDC 30068, Fauhaber). A LabVIEW program (National Instruments) was used for data acquisition and parameter control. The DAQ box was the NI 6009 (National Instruments).

The schematic setup for the tests is presented in FIG. 9 showing a schematic representation of a measurement setup. The different fluid ways for flow rate (I), pressure (II) and fatigue (III) experiments are marked with numbers and colored ways.

Tests were made to determine the characteristics of the peristaltic pump. A test stage, according to FIG. 9 (I), consisting of a fluid reservoir, the fluid connectors and the particular test stage was created.

The objective of the test was to investigate the dependency of the flow rate from inner tube diameter and circumferential speed. With the scope of small volumes, the circumferential speed was set between 24 and 72 rpm. Two fluids were tested partly with tubes of an inner diameter of 0.3 mm, 0.4 mm, 0.7 mm and 0.8 mm. The pump was started for 60 seconds at different circumferential speeds and the transported liquid has been collected and scaled. Every dosage step was repeated at least six times for higher accuracy. The weight was divided by the number of rotations and the number of rollers to obtain the single dosage volume.

FIG. 10 shows a graphical representation of the flow rate depending on inner tube diameter (water). A near linear developing of the values can be seen as expected for a positive displacement pump. A minimum single dosage volume of around 0.3 µl was measured for the tubes with $d_i$=0.4 mm diameter. The maximum volume of around 1.81 µl per ⅓ revolution step was found for the 0.8 mm inner diameter tubes.

Mean variation is slightly higher for the lower values of 24 and 36 rpm. The coefficient of variation (COV) is between 1.02 and 4.8 percent for all speeds. The COV is lower for smaller inner diameters, possibly caused by lower fluctuations (Gilson, httpi/www.seas.upenn.edu/~belab/equipment/equipment_links/Minipuls3_.Manual.pdf, acquired 23.10.2015).

No fluid transport was measured with the 0.3 mm tubes. It is assumed, that the ratio of inner to outer diameter led to a very high stiffness of the tube and disadvantageous bending behavior of the material. A comparison with the measured single volumes and previous calculated values shows a difference already of about 20 percent for the 0.4 mm tube, which sup-ports the occlusion theory. Another aspect Is the over proportional reduced volume in a pumping chamber, due to the different wall thickness of all tubes (same outer diameter of 1.2 mm). A reduction of the outer diameter and tests with a linear arrangement will be carried out in future to overcome this problem and to achieve even smaller volumes The investigations of the glycerin mixture behavior (not shown) present the same results. The coefficient of variation is lower for all measurements compared to the water results (<0.67 percent).

The maximum pressure generated by the pump was carried out with the setup according to FIG. 8 (II). After activating the pump and closing the valve, the occurring pressure was measured. The circumferential speed was varied for different tests between 60 and 180 rpm. The test liquids were the previous used water and glycerin water mixture. The glycerin mixture was chosen due to the higher viscosity to reduce a possible backflow. Pump cartridges with the tube diameter of 0.7 mm have been used during the tests.

For the lower rotor speed of 60 rpm and water, a maximum pressure of approximately p=3.0 bar was measured. The glycerin mixture led to about p=3.5 bar. In the next tests the speed was increased unless a pressure of p=5.5 bar was achieved with the glycerin mixture and 180 rpm. This is a pumping head of 55 m. The corresponding result for distilled water was p=4.8 bar, with another pump cartridge. The high pressure remained stable unless the motor was stopped. The differences are caused by the higher viscosity of the glycerin mixture that leads to a reduced backflow.

FIG. 11 shows the diagram for the maximum pressure measurement. It is to be noted, that the time necessary to obtain that pressure was around 100 seconds due to the large dead volume after the pump. Several connectors, partly flexible pipes and the pressure sensor adapter reduced the dynamic of the pump.

Better connectors and stiff pipes or the implementation into the LOC will lead to a higher performance. More detailed investigations will be addressed on the effects of the wall thickness/inner diameter ratio and the rotation speed dependency. Also very interesting is the dependency of pressure fluctuations due to the pumping principle and wall thickness or tube material.

The fatigue behavior was investigated to identify the application spectrum of the micro pump. The test was carried out at a speed of 100 rpm. The cartridge was inserted into the bracket and connected with PTFE tubes. A fluid reservoir granted the circulation mode of the test liquid. The pressure sensor measured the adjacent pressure at the outlet of the pump. A pressure drop below a certain level, detected by the LabVIEW program would lead to a stop of the test. The set-up is shown in FIG. 8 (III).

Two tube diameter with one (0.4 mm) and two (0.7 mm) samples were tested for 50,000 rotations of the rotor. This led to 150,000 occlusions and chum movements of the tube. The flow rate was tested exemplary with water after the fatigue investigation, to detect a damaging of the tube.

No wear effects were found during the investigations. The flow rate tests after the fatigue tests have shown no significant difference compared to the single flow rate investigation.

A modular micro fluidic peristaltic pump has been shown, where the complete contaminated disposable pump cartridge can be discarded after usage. Pipes, stiff PTFE tubes or other fluidic components can be easily connected via flexible ports and sealing ends. It provides the opportunity for a high pressure generation and a small single dosage volume in the nano liter range.

The fatigue resistance of the tubes was high. Over eight hours of continuous operation will be more than enough for any LOC application. The real fatigue limit will be tested in future.

The micro pump can be carried out as a stand-alone or an on chip device. Its small size suits to the requirements of low dead volume and high system integration.

Injection molding of the simple geometries of housing and tube allow the reasonable mass production of the peristaltic micro pump.

FIG. 12 shows a schematic representation of an alternative disposable cartridge for a peristaltic micro pump provided with the channel section 40 of a fluid channel, the channel section 40 provided by a flexible tube. It may be provided as a micro fluidic mixing chip (e.g. dimensions of 20×40 mm). The channel section 40 provides for a curved tube section configured to engage, through a respective opening in the housing, with pump engaging elements providing a rotating pump element arrangement (see FIG. 2 to 4).

The presented approach allows the simple integration of a tube and therefore a peristaltic micro pump into a μTAS device (TAS—Total Analysis System).

FIG. 12 shows an embodiment with a circular flexible tube alignment geometry. There are two inlet ports 42, 43 which allow the attachment of external tubes or reservoirs. The processed volume leaves the device through an outlet port 44. The rotor of the circular pump swings into an opening 46 of the housing 21 to actuate the curved flexible tube section of the fluid channel 40 provided in the housing 21.

Alternatively or additionally, a linear flexible tube alignment geometry (see FIGS. 6 and 7) may be provided. In this case, the linear actuator (pump engaging elements) operates the linear flexible tube section from above through an opening in the upper part of the chip housing (not shown). When more than one tube alignment geometry is provided, each tube alignment geometry may be assigned to one inlet port 42, 43.

FIG. 13 shows a schematic representation of an alternative embodiment of a disposable cartridge for a peristaltic micro pump provided with a channel section 40 of a fluid channel, the channel sections 40 provided by a flexible tube. The channel section 40 provides for a curved tube section configured to engage, through a respective opening in the housing, with the pump engaging elements providing a rotating pump element arrangement (see FIG. 2 to 4). This approach also allows the simple integration of a tube and therefore a peristaltic micro pump into a μTAS device (TAS—Total Analysis System). In this embodiment, a wrap angle of the flexible tube is varied in comparison with the cartridges shown in FIG. 2 to 4. Additionally, the flexible tube is provided with holding elements 60 to prevent moving or twisting of the flexible tube when pump engaging elements are engaged. Recesses 61 are provided for coupling the cartridge to a peristaltic micro pump The features disclosed in this specification, the figures and/or the claims may be material for the realization of various embodiments, taken in isolation or in various combinations thereof.

The invention claimed is:

1. A disposable cartridge for a peristaltic micro pump, comprising
    a housing configured to detachable mount to a peristaltic micro pump;
    an inlet provided on the housing and comprising an inlet connector;
    an outlet provided on the housing and comprising an outlet connector;
    a fluid channel extending in the housing between the inlet and the outlet;
    a channel section of the fluid channel, the channel section provided by a flexible tube; and one or more openings in an exterior surface of the housing adjacent to the channel section in the housing and open on a narrow side of the housing, thereby exposing the flexible tube to an exterior of the housing in such a way that one or more pump engaging elements of a pump drive can engage with the flexible tube through the one or more openings for compressing the flexible tube in a pumping process for pumping a fluid through the fluid channel;

wherein the flexible tube comprises at least one sealing element on each of opposite sides, wherein the sealing elements are provided with double flange extensions each with a first, inner flange for fixing the flexible tube in the housing and a second, outer flange for sealing connection at the inlet connector and the outlet connector, respectively, and also for fixing the flexible tube in the housing.

2. The disposable cartridge according to claim 1, wherein the flexible tube is detachably received in a tube recess of the housing.

3. The disposable cartridge according to claim 1, wherein the flexible tube comprises at least one of a curved tube section and a linear tube section configured to engage with the one or more pump engaging elements providing a rotating pump element arrangement, and a linear pump element arrangement, respectively.

4. The disposable cartridge according to claim 3, wherein the housing comprises a curved housing section for receiving the one or more pump engaging elements of the rotating pump element arrangement provided on a rotor within the curved housing section, wherein a first opening is provided adjacent to the curved section in a rotor recess.

5. The disposable cartridge according to claim 4, wherein the first opening is provided on the narrow side of the housing.

6. The disposable cartridge according to claim 1, wherein the flexible tube comprises a plurality of flexible sub-tubes, each of the flexible sub-tubes received in a separate sub-recess of the housing and providing for a channel sub-section of the fluid channel.

7. The disposable cartridge according to claim 1, wherein the flexible tube is form-fitted received in a recess.

8. The disposable cartridge according to claim 1, further comprising a fluid reservoir provided in the housing and having a fluid connection to the fluid channel.

9. A peristaltic micro pump, comprising a disposable cartridge according to claim 1.

* * * * *